US008147804B2

(12) United States Patent
Roesch et al.

(10) Patent No.: US 8,147,804 B2
(45) Date of Patent: Apr. 3, 2012

(54) METHOD AND DEVICE FOR ISOLATING A CHEMICALLY AND RADIOCHEMICALLY CLEANED $^{68}$GA-RADIONUCLIDE AND FOR MARKING A MARKING PRECURSOR WITH THE $^{68}$GA-RADIONUCLIDE

(75) Inventors: Frank Roesch, Zornheim (DE); Dmitry V. Filosofov, Dubna (RU); Konstantin Zhernosekov, Garching (DE); Marc Jennewein, Mainz-Kastel (DE)

(73) Assignee: Johannes Gutenberg-Universität Mainz, Mainz (DE)

( * ) Notice: Subject to any disclaimer, the term of this patent is extended or adjusted under 35 U.S.C. 154(b) by 1082 days.

(21) Appl. No.: 11/719,981

(22) PCT Filed: Nov. 22, 2005

(86) PCT No.: PCT/EP2005/012471
§ 371 (c)(1),
(2), (4) Date: Jan. 24, 2008

(87) PCT Pub. No.: WO2006/056395
PCT Pub. Date: Jun. 1, 2006

(65) Prior Publication Data

US 2008/0277350 A1 Nov. 13, 2008

(30) Foreign Application Priority Data

Nov. 26, 2004 (DE) ......................... 10 2004 057 225

(51) Int. Cl.
*A61K 49/04* (2006.01)

(52) U.S. Cl. ...... 424/9.4; 424/1.11; 424/1.49; 424/1.65; 424/1.69

(58) Field of Classification Search ................. 424/1.11, 424/1.49, 1.65, 1.69, 9.1, 9.3
See application file for complete search history.

(56) References Cited

FOREIGN PATENT DOCUMENTS

| | | | |
|---|---|---|---|
| GB | 2056471 A | * | 3/1981 |
| GB | 2 067 343 A | | 7/1981 |
| WO | WO 99/49935 A1 | | 10/1999 |
| WO | WO-03059397 | * | 7/2003 |

OTHER PUBLICATIONS

R.M. Wheaton and W.C. Bauman, Properties of Strongly Basic Anion Exchange Resins, Industrial and Engineering Chemsity, 1951, 43, 1088-1093.*

Tjaart N. Van der Walt et al. Quantitative Separation of Gallium from other elements by Cation-Exchange Chromatograpy, Anal. Chem. 55, 212-216, 1983.*

Instruction Manual BIO_RAD pp. 1-28, 2000.*

Nakayama M et al.: "A new $^{68}$ Ge/$^{68}$ Ga generator system using an organic polymer containing N-methylglucamine groups as adsorbent for $^{68}$ Ge" Applied Radiation and Isotopes Elsevier UK, vol. 58, No. 1, Jan. 2003, pp. 9-14.

Gleason G I: A positron cow International Journal of Applied Radiation and Isotopes UK, vol. 8, No. 2-3, Jul. 1960, pp. 90-94.

Loc'H et al.: "A new generatorfor ionic gallium-68" Journal of Nuclear Medicine USA, vol. 21, No. 2, Feb. 1980, pp. 171-173.

Broadack J W et al.: "Laboratory robotics for the remote synthesis of generator-based positron-emitting radiopharmaceuticals" Laboratory Robotics and Automation USA, vol. 1, No. 5-6, Sep. 1989, pp. 285-294.

Velikyan I et al.: "Preparation and evaluation of $^{68}$ Ga-DOTA-Hegf for visualization of EGFR expression in malignant turmors" Journal of Nuclear Medicine Soc. Nucl. Med USA, vol. 46, No. 11, Nov. 2005, pp. 1881-1888.

Nakayama M ett al.: "Separation of $^{68}$Ge from $^{68}$Ga using a macroporous organic polyer containing N-methylglucamine groups" Analytica Chimica Acta, Elsevier, Oxford, GB, vol. 453, 2002, pp. 135-141.

* cited by examiner

*Primary Examiner* — Michael G Hartley
*Assistant Examiner* — Jagadishwar Samala
(74) *Attorney, Agent, or Firm* — ProPat, L.L.C.

(57) ABSTRACT

The invention relates to initial $^{68}$Ge/Ga-generator elute which is guided directly to a cation exchanger, whereon $^{68}$Ga is quantitatively absorbed and is cleaned simultaneously in a chemical and radio chemical manner. Subsequently, the $^{68}$Ga-radio nuclide is combined with a radio pharmaceutical substance by a marking precursor made of a ligand or a peptide or a protein which is cross-linked in a covalent manner to a ligand.

26 Claims, 2 Drawing Sheets

METHOD AND DEVICE FOR ISOLATING A CHEMICALLY AND RADIOCHEMICALLY CLEANED $^{68}$GA-RADIONUCLIDE AND FOR MARKING A MARKING PRECURSOR WITH THE $^{68}$GA-RADIONUCLIDE

CROSS-REFERENCE TO RELATED APPLICATIONS

This application is being filed under rule 1.371 as a National Stage Application of pending International Application No. PCT/EP2005/012471 filed Nov. 22, 2005, which claims priority to the following parent application: German Patent Application No. 10 2004 057 225.9 filed Nov. 26, 2004. Both International Application No. PCT/EP2005/012471 and German Patent Application No. 10 2004 057 225.9 are hereby reference herein in their entirety.

FIELD OF THE INVENTION

The invention relates to a method and a device for isolating a $^{68}$Ga radionuclide from a $^{68}$Ge/Ga generator and for labelling a labelling precursor with the $^{68}$Ga radionuclide into a radiopharmaceutical.

BACKGROUND OF THE INVENTION

The positron-emitting $^{68}$Ga radionuclide with $T_{1/2}$=68 min is of enormous practical importance for clinical positron emission tomography (PET). For the generation of radionuclides known radionuclide generators are used, the obtained daughter radionuclides generally having short half-lives $T_{1/2}$ in comparison to their parent radionuclides.

Radionuclide generators like these are based on a concept of the effective radiochemical separation of decaying parent and daughter radionuclides in such a manner that the daughter nuclide should be obtained in a form with the greatest possible radionuclidic and radiochemical purity.

In comparison to the in-house radionuclide production systems such as accelerators or nuclear reactors, the availability of short-lived radionuclides from radionuclide generators offers an inexpensive and simpler alternative.

The development of radionuclide generators over the past three decades was always marked by the growing range of applications of radionuclides and labelled agents in medicine, especially, for nuclear-medicine diagnostics and therapy. In addition, in recent years, many promising applications of generator-based therapeutic radionuclides in nuclear medicine, oncology and cardiology were developed. This growing importance of radionuclide generators has stimulated a broad development in the production of radionuclides for radionuclide generators, for adequate radiochemical separations as well as for a reliable technical design of radionuclide generator systems. The first generator for applications in the life sciences was already developed in 1920 and via $^{226}$Ra ($T_{1/2}$=1.60·10$^3$ a) made available the daughter $^{222}$Rn ($T_{1/2}$=3.825 d) for the production of radon seeds for radiation therapy.

But radionuclide generators did not attain to practical significance until 1951 in the form of the $^{132}$Te($T_{1/2}$=3.26 d)/$^{132}$I ($T_{1/2}$=1.39 h) generators, and to a much more significant extent in 1957 by the pioneering development of the $^{99}$Mo/$^{99m}$Te generators (Stang et al. 1954, 1957). The potential of the daughter nuclide technetium for medical uses quickly became clear and, indeed, the first clinical applications were already described in 1961 which since that time have revolutionized radiopharmaceutical chemistry and nuclear medicine.

The widespread use of the $^{99}$Mo/$^{99m}$Te generator system in nuclear medicine is a typical example of the significance of radionuclide generators for clinks and radiopharmaceutical manufacturers for a broad range of diagnostic radiopharmaceuticals. More than 35,000 diagnostic studies daily with $^{99m}$Te involving more than 12 million applications annually are estimated to be conducted just in the USA alone.

Radionuclide generator developments have often ben systematized. Detailed reports about these have devoted themselves to various aspects: parent-daughter half-lives, reactor-produced nuclides, accelerator-produced nuclides, cyclotron production of generator nuclides, ultra-short-life generator-produced radionuclides, generator-based positron-emitting radionuclides, clinical applications.

In the meantime, various other generator systems were developed and some of them have attained to significant practical importance. At present, $^{68}$Ge($T_{1/2}$=270.8 d/$^{68}$Ga ($T_{1/2}$=68 min) generator systems dominate the prior art. Various separation types, $^{68}$Ga yields and $^{68}$Ge contents are specified below.

The initial generator systems separated $^{68}$Ga as an EDTA complex from $^{68}$Ge, which was absorbed onto alumina or zirconium oxide, the resulting neutral [$^{68}$Ga]EDTA solution acting to image tumors. According to an analogous concept $^{68}$Ge was retained on antimony oxide $Sb_2O_5$ and $^{68}$Ga eluated using oxalate solutions. Anion-exchange resins and thinned HF solutions as eluents permitted highly effective separations due to the significant differences of the distribution coefficients of the elements. The $^{68}$Ge breakthrough was under $10^{-4}$ percent for as many as 600 elutions; the $^{68}$Ga yield was greater than 90%.

In all these generator systems a further direct use of the generator eluate for $^{68}$Ga labellings was not possible. For this reason, $^{68}$Ge/$^{68\ Ga}$ generators were developed which led to ionic $^{68}Ga^{3+}$ eluates. In these cases $^{68}$Ge was fixed onto inorganic matrices such as alumina $Al(OH)_3$ and $Fe(OH)_3$, onto $SnO_2$, $ZrO_2$, $TiO_2$ or $CeO_2$. Tin(IV) oxide $SnO_2$ presented the best parameters in terms of $^{68}$Ge breakthrough ($10^{-6}$-$10^{-5}$% per bolus) and the $^{68}Ga^{3+}$ elution yield (79-80%) in 1 M HCl. Since Ge(IV) is known to form stable complexes with the phenol group, the $^{68}$Ge(VI) adsorption onto 1,2,3-trihydroxybenzene(pyrogallol) formaldehyde resins was also exploited. Thus, for a 370 MBq (10 mCi) generator $^{68}Ga^{3+}$ elution yields greater than 50% and $^{68}$Ge breakthroughs lower than 0.01 ppm were described in the course of the first utilizations.

The $^{68}$Ge content defines the radiochemical purity of the separated $^{68}$Ga fraction. Even an initial contamination of some $10^{-2}$%, corresponding to, for example, 1 μCi $^{68}$Ge in a $^{68}$Ga fraction of a 10 mCi $^{68}$Ge/Ga generator system, appears to be already borderline in connection with a subsequent medical application.

$^{68}$Ga eluate volumes and chemical purity are other decisive values for the use of $^{68}$Ga to synthesize radiopharmaceuticals.

In all the current commercially available $^{68}$Ge/Ga generator systems elution volumes of several ml of different HCl solutions are necessary. In addition to considerable volumes, the chemical purity of these $^{68}$Ga eluates is an additional critical aspect of $^{68}$Ge/Ga generator systems.

The highest chemical purities, especially a minimum content of diverse metallic cations, are necessary for efficient labelling reaction with high yields. This applies especially in cases where labelling chemistry is conceived making use of bifunctional chelators. In this context, even small amounts of stable $^{68}$Zn as a direct decay product of $^{68}$Ga, of titan, in cases whether the $^{68}$Ge/Ga generator system ion exchanger column is made of $TiO_2$, and especially also of iron, can prevent high labelling yields.

At present, commercially available $^{68}$Ge/Ga generator systems are limited to effective $^{68}$Ga elutions and do not comprise modalities for volume minimizing and purification of the generator eluates or labellings of potential radiopharmaceuticals.

Initial volumes of the eluates amount to from a few ml to 10 ml of HCl solutions of various concentrations. Both the labelling reactions as well as the filling of balloons generally require smaller volumes of roughly 0.5 ml to 0.1 ml. Hence, chemical or technological strategies are necessary which immediately afterwards the initial generator elution lower the eluate volume.

Secondly, the generator eluate can contain chemical and radiochemical contaminations which prevent the efficient exploitation of radiochemical labels with high yield. These chemical contaminations can come from:

- the generator column material (for example $TiO_2$);
- trivalent Fe, which is ubiquitous in traces and can especially be introduce with diverse electrolytes during the manufacture or use of the generator;
- $^{68}$Zn as a stable metallic contamination, which system-inherent is continuously generated as a decay product of $^{68}$Ga on the generator column;
- $^{68}$Ge as parent radionuclide, whereby even slight contaminations of less than 0.01% of the $^{68}$Ge in the eluate represent a similar number of atoms as the $^{68}$Ga itself, and which can act in a radiotoxic and chemotoxic manner.

Besides the aspect of the chemical contaminations by $^{68}$Ge in the generator eluate, this contamination is also radiochemically relevant, especially in view of the potential medical applications. Hence, the post-elution procedure should explicitly comprise a chemical strategy for the further separation of the $^{68}$Ge.

Thirdly the $^{68}$Ga labelling of potential radiopharmaceutical assumes a central role for which the corresponding chemical reaction parameters must be optimized.

The trivalent Gallium hydrolyzes already from pH>2 and has a marked tendency to absorb on the surfaces of glass and polymers at pH>3, especially in the condition of the low $^{68}$Ga concentrations (no-carrier-added), as they arise from the generator system. Finally, special reaction conditions must be chosen in the case of the labelling chemistry of targeting vectors using bifunctional chelators such as DOTA due to the complexing kinetics as well as due to the aqueous chemistry of the Ga(III) cation.

In addition to the metallic contaminations associated with the operation of the generator system which are eluated along with the $^{68}$Ga, the contaminations contained in the buffer systems generally used for $^{68}$Ga labels can in some cases also handicap high labelling yields.

Processes related to solvent vaporization for the reduction of volumes of generator eluates or of the final solutions of the $^{68}$Ga radiopharmaceutical an also lead to losses of activity both owing to the related longer duration of the process as well as owing to adsorption losses along the vessel walls.

Individual experimental conceptions towards the minimization of the eluate volume for $^{68}$Ge/Ga generator systems have been developed. Some of these realizations (Meyer et al. 2004, Velikyan et al. 2004) minimize the initial eluate volumes by mixing with several ml of concentrated HCl, whereby a total of 6 M HCl solution of an increased volume of approximately 15 ml results. This large volume is then transferred to an anion-exchanger column on which the $^{68}$Ga is adsorbed. Then the $^{68}$Ga is eluated with less than 1 ml water. Although this time-consuming procedure does realize a reduction in the volume of the $^{68}$Ga fraction, there is no obvious parallel strategy for separating chemical contaminations out of the initial generator eluate.

Subsequently, 10-20 nmol DOTATOC is then added to this fraction in a small volume of an aqueous 1 M HEPES or other buffer solution. Here too, potential contaminations by the concentrated buffer system cannot be excluded.

These factors can be the reason for the fact that the labelling yields of $^{68}$Ga-DOTATOC and analogous compounds achieved under standard heating protocol have been merely 58±20% (Meyer et al. 2004). Greater yields are described by microwave-supported heating (Velikyan et al. 2004).

Overall, none of the currently commercially available generator systems comprise the corresponding chemical or technological strategies to solve the problems mentioned as a whole.

The problem of the invention is to create a method and a device which makes available highly pure $^{68}$Ga eluate which is largely free of chemical and radiochemical contaminations with a high yield and very low eluate volume. In the framework of this problem the chemical reaction parameters such as the pH value of the $^{68}$Ga for the labelling of the labelling precursors should also be optimized. Furthermore, a procedure for labelling potential radiopharmaceuticals for positron emission tomography should be provided.

At the same time, all the process steps should meet the requirements of simple and routine use in a medical environment.

SUMMARY OF ADVANTAGEOUS EMBODIMENTS OF THE INVENTION

This problem is solved by a method in which initial $^{68}$Ge/Ga generator eluate is directly fed into a cation exchange and $^{68}$Ga is absorbed quantitatively on the cation exchanger, at the same time chemically and radiochemically purified at the $^{68}$Ga radionuclide is combined with a labelling precursor comprising a ligand or a peptide or protein covalently cross-linked with a ligand into a radiopharmaceutical.

In a development of the method, the cation exchanger is chosen from the group of highly acidic cation exchangers polystyrene/divinylbenzene (DVB) resins with a DVB amount of 2 to 20% in reference to the cross-linked polymers of the resins, and the matrix of the cation exchanger is loaded with $^{68}$Ga. The sulfonated polystyrene/divinylbenzene (DVB) resins have a gel-type structure and feature permanently negatively charged sulphonic acid groups. Each of these active groups has a fixed electrical charge and is in balance with a number of ions with the equivalent opposite charge which are free to be exchanged with other ions with the same charge.

Already during the absorption of $^{68}$Ga on the cation exchanger a chemical purification occurs in that the initial eluated $^{68}$Ge is not adsorbed and, hence, the radiochemical $^{68}$Ge contamination is reduced to a value less than $10^{-8}$ percent.

Carrying out the method, the $^{68}$Ga fraction adsorbed on the cation exchanger continues to be purified with acidic solutions of the type HCl/acetone or HCL/ethanol or analogous systems in such a manner that chemical contaminations such as FE(II) and Zn(II) are eluated from the cation exchanger. During the elution, the $^{68}$Ga radionuclide remains completely on the cation exchanger, and a substantial separation occurs from the initial eluate (Ti(IV).

The chemically and radiochemically pure $^{68}Ga$ radionuclide produced by the elution can be used directly for the synthesis of radiopharmaceuticals.

The further improvement of this method results from the features of the patent claims 6 to 16.

DETAILED DESCIPTION OF ADVANTAGEOUS EMBODIMENTS OF THE INVENTION

The device for the isolation of a chemically and radiochemically purified $^{68}Ga$ radionuclide from a $^{68}Ge/Ga$ generator eluate and for the labelling of a labelling precursor with the $^{68}Ga$ radionuclide comprises in improvement of the invention a conveyance apparatus connected by means of a conduit to a $^{68}Ge/Ga$ generator, a number of conveyance apparatuses for the purification of the $^{68}Ga$ fraction adsorbed on a cation exchanger, a synthesis apparatus into which a conduit leads from the outlet of the cation exchanger, and in which the $^{68}Ga$ radionuclide and the labelling precursor are converted to a radiopharmaceutical, as well as a cartridge for the purification of the radiopharmaceutical at whose inlet conveyance apparatuses are connected via conduits and whose outlet is connected via a 3-way valve to a conduit leading out of the synthesis apparatus, a reservoir and a product vessel to hold the radiopharmaceutical.

Figure 1:
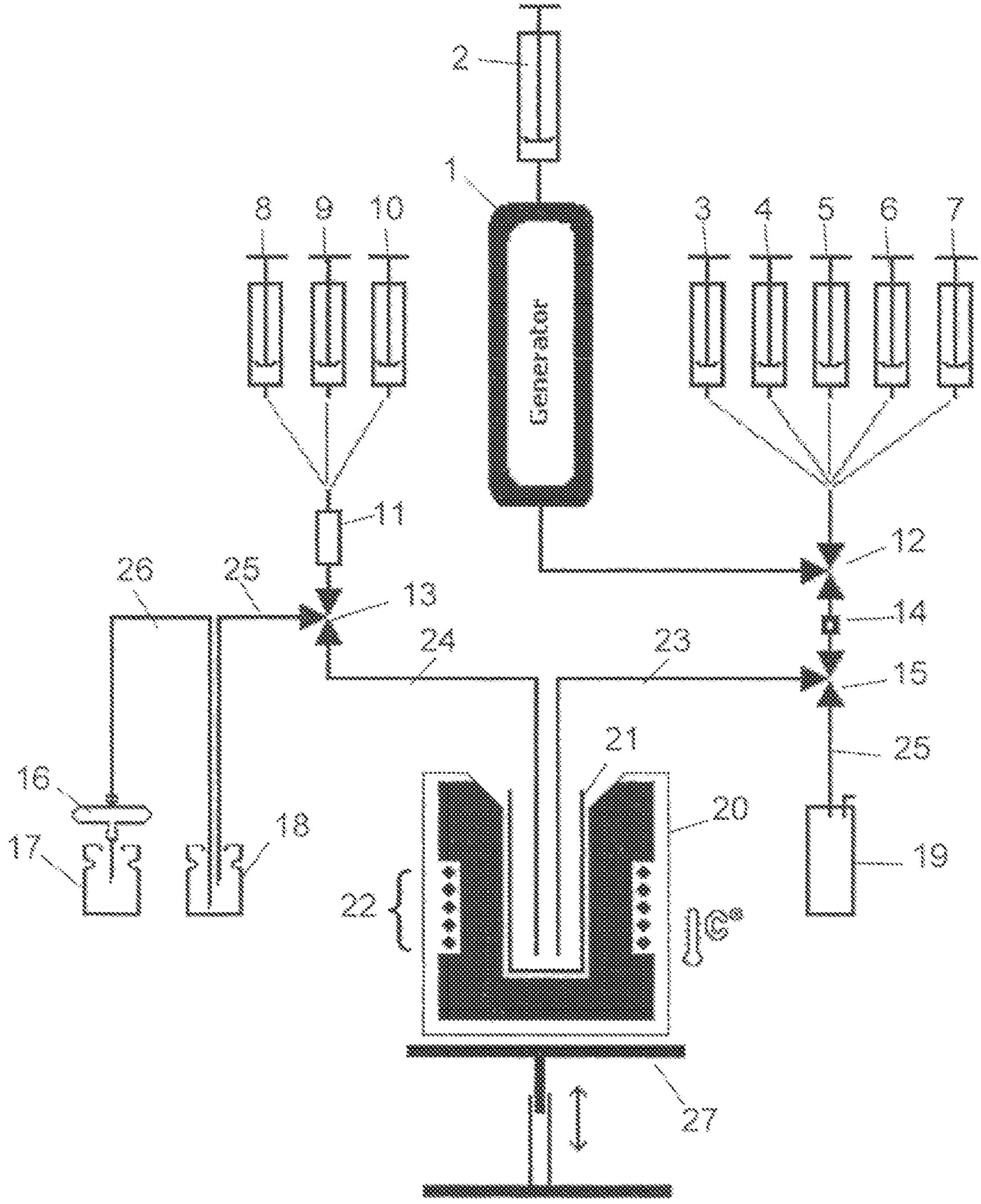
FIG. 1 is a schematic illustration of an exemplary devive according to the invention and FIG. 2 is a flow chart of an exemplary method of operation of an advantageous device.
Figure 2:
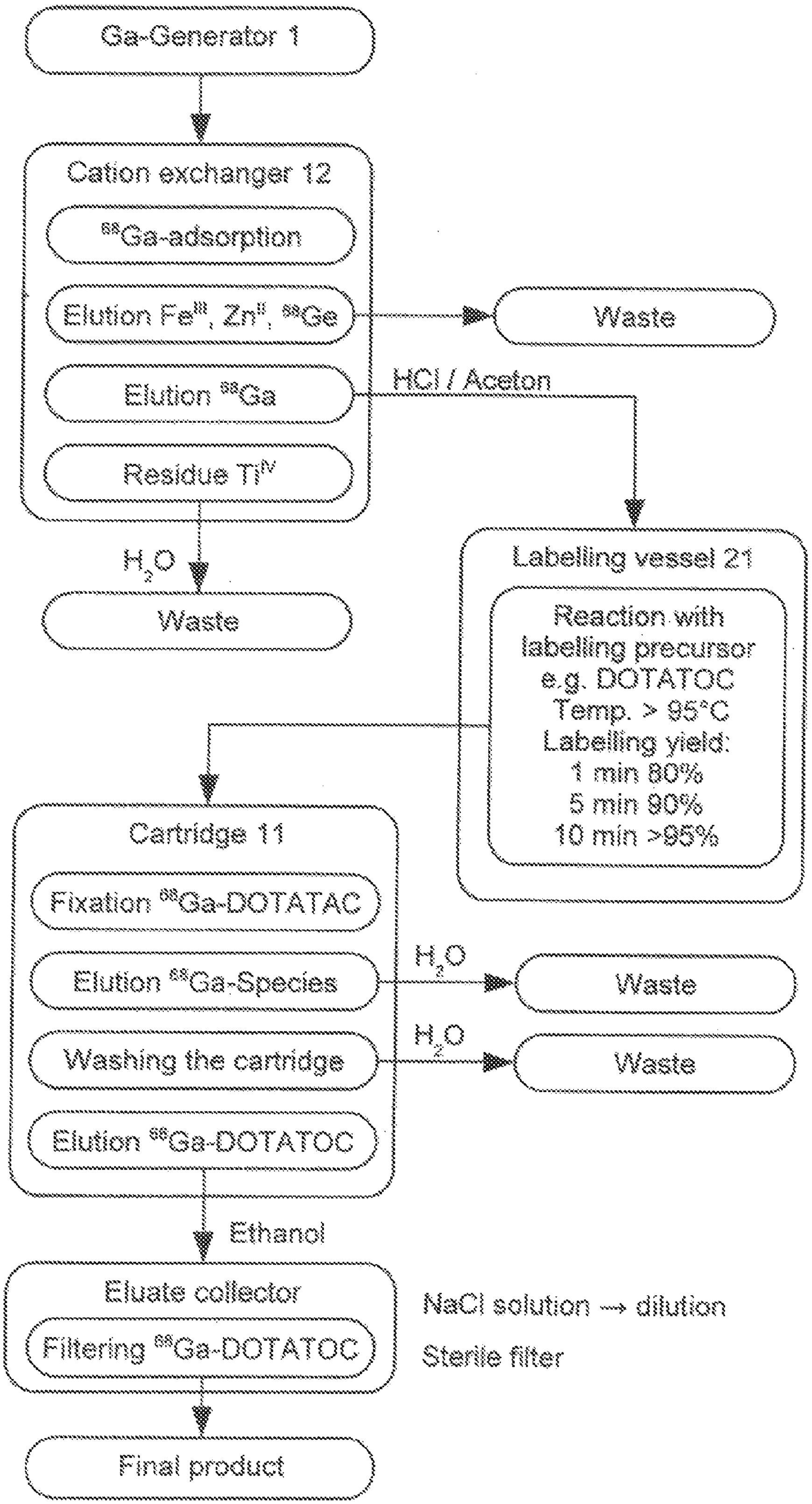

By FIGS. 1 and 2 the device and its method of operation for the isolation of a $^{68}Ga$ fraction from a $^{68}Ge/Ga$ generator, its purification and volume reduction for obtaining the $^{68}Ga$ radionuclide, as well as labelling the labelling precursors with the purified $^{68}Ga$ radionuclide is described. Shown are in:

FIG. 1 a schematic drawing of the device according to the invention, and

FIG. 2 the flow chart of the method of operation of the device.

Corresponding to the relatively short half-life of 68 min of the $^{68}Ga$, the whole procedure of the generator elution, purification, volume reduction, as well as labelling must be optimized: every 10 minutes, more than 10% of the $^{68}Ga$ radioactivity decays. Many of the currently established generator systems with subsequent labelling reaction require up to one hour until the completion of the whole procedure. Alternative methods with, for example, the half of this overall time already mean a significant increase in the final radioactivity of the $^{68}Ga$ labelled radiopharmaceutical. This is especially relevant because this can also have the consequence of a corresponding minimization of the initially required $^{68}Ge$ activity of the generator system which impacts as a cost factor.

The device according to FIG. 1 comprises a $^{68}Ge/Ga$ generator 1, which via conduit is connected downstream from a conveyance apparatus 2, for example i the form of a piston, a syringe or a peristaltic pump (roller-wheel tube pump). The conveyance apparatus 2 is connected in a manner not shown with a liquid-filled storage means or reservoir if a roller-wheel tube pump is involved. In the case of a piston or a syringe these are directly filled with a liquid. The outlet of the generator 1 is connected by means of a first 3-way valve 12 to the cation exchanger 14 at the inlet end. Furthermore, the conveyance apparatuses 3, 4, 5, 6, 7 are connected by means of conduits to the 3-way valve 12. For these conveyance apparatuses, as well as for the following described conveyance apparatuses, the statements made apply equally to the conveyance apparatus 2. In place of a 3-way valve, a multi-way slide valve can also be used. It is also possible to install open-shut valves or cocks which variably open the individual conduit as necessary or completely open or completely shut.

Preferably, in a manner not shown, several $^{68}Ge/Ga$ radionuclide generators are eluated simultaneously or sequentially and the common initial eluates are fed to the cation exchanger. 14. The $^{68}Ge/Ga$ generators can in this context also continue to be operated or used if their initial $^{68}Ga$ eluate already contains an unacceptably high level of $^{68}Ge$. This extends the usable life of a $^{68}Ge/Ga$ generator significantly, especially for generators with 50 or more mCi $^{68}Ge$.

The cation exchanger 14 is connected to a second 3-way valve 15 at the output end. A conduit 25 leads from the 3-way valve 15 to a waste vessel 19, another conduit 23 leads from the 3-way valve 15 into a labelling vessel 21 which is arranged in a synthesis apparatus 20 of the device. The heatable synthesis apparatus 20 is equipped with a heating unit 22 and sits on a vertically adjustable table 27. By lowering the table 27 the access to the labelling vessel 21 is made easier. The components of he device described to this point contribute to the isolation of the $^{68}Ga$ eluate, its volume reduction and purification. Instead of a vertically adjustable table, a stable slab can support the synthesis apparatus 20, and equally a sliding carriage lateral traveling on rails or rollers.

A conduit 24 leads from the labelling vessel 21 to a third 3-way valve 13. The 3-way valve 13 is connected at the input end to a cartridge 11. Moreover, from the 3-way valve 13 a conduit 25 leads to a reservoir 18 for the purified labelling agent. An additional conduit 26 connects the reservoir 18 to the product vessel 17. In this conduit 26 a filter 16 is arranged ahead of the input into the product vessel 17. In product vessel 17 the radiopharmaceutical is made available for administration and can be removed from it at any time.

The unit comprising the filter 16, product vessel 17, conduit 26 enables sterile filtration which involves an independent process step which can be carried out in isolation. Hence, if necessary, the unit 16, 17 can be disconnected from the overall device and be operated independently.

The method of operation of the device is described with the help of the flow chart shown in FIG. 2.

From the conveyance apparatus 2 pressure is exerted in a manner not shown on the eluent for the initial $^{68}Ge/Ga$ generator elution from the $^{68}Ge/Ga$ generator 1. The eluate moves via the first 3-way valve 12 onto the cation exchanger 14 and continues via the components 15 and 25 into the vessel 19.

The cation exchanger is a highly acidic cation exchanger from the group of polystyrene/divinylbenzene (DVB) resins with a DVB amount of 2 to 20% in reference to the cross-linked polymers of the resins. The sulphonated polystyrene/divinylbenzene (DVB) resins have a gel-type structure and feature permanently negatively charged sulphonic acid groups. Each of these active groups has a fixed electrical charge and is in balance with a quantity of ions with the equivalent opposite charge which are free to be exchanged with other ions with the same charge.

First, on the cation exchanger 14 $^{68}Ga^{3+}$ is adsorbed which initially is contaminated with, among other substances, Fe(III), Zn(II), Ti(IV) and $^{68}Ge$. Simultaneously, during this process, the $^{68}Ge$ fraction contained therein is removed.

This is followed by the elution of the fractions of Fe(III) and Zn(II) which were adsorbed together with $^{68}Ga$ on the cation exchanger. For this purpose, the conveyance apparatuses 3 compresses an acidic solution consisting of HCl/acetone or HCl/ethanol or analogous systems through the first 3-way valve 12 into the cation exchanger 14 and Fe(III) and Zn(II) are flushed out and conducted through the second 3-way valve 15 into the waste vessel 19. Subsequently, the conveyance apparatus 4 compresses air through the conduits in order to flush them and remove any residues of Fe(III) and Zn(II).

In the following step the conveyance apparatus 5, which is filled with a second acidic solution consisting of HCl/acetone or HCl/ethanol or analogous systems, feeds this solution through the 3-way valve 12 to the cation exchanger 14 and by means of this acidic solution $^{68}$Ga is eluted from the cation exchanger and fed through the 3-way valve 15 and conduit 23 into the labelling vessel 21.

Subsequently, the conveyance apparatus 4 again compresses air through the conduits to flow them and collect any residues of $^{68}$Ga nd feed them into the labelling vessel 21. The described processes effectuate that the Ti(IV) initially eluted by the generator cannot enter the labelling vessel together with the $^{68}$Ga fraction which means a further chemical purification.

At an appropriate time, the residues of Ti(IV) still present on the cation exchanger 14 are first flushed from the conveyance apparatus 6 with HCl and fed into the waster vessel 19; subsequently, the cation exchanger is washed with water from conveyance apparatus 7, which readies the cation exchanger finally for a new procedure.

The labelling vessel can either be empty and then be used for the filling of balloons with the now minimized volume of $^{68}$Ga for the synthesis of radiopharmaceuticals. The latter use is described below:

In the labelling vessel 21 the labelling precursor is labelled with purified $^{68}$Ga radionuclide to form the radiopharmaceutical. This precursor consists of a ligand, or a peptide or protein cross-linked in a covalent manner with a ligand, or another component, whereby the $^{68}$Ga radionuclide is chemically bonded by the ligand. The ligand is selected from, among others, the group of linear or cyclical polyamine polycarboxylic acids (DTPA, EDTA or DOTA, among others) or others, including ligand structures containing phosphorous and sulphur as donor atoms, the peptide from the group octreotide, bombesin, gastrin and many more others, whereby the respectively selected peptide has a highest possible affinity with tumor cells, specifically with the tumor cell membrane surface receptors as well as with receptors on other organs. Analogously modified proteins can be used in the form of antibodies for binding to tumor antigens.

For the reaction of the $^{68}$Ga radionuclide with the ligand of the labelling precursor, a certain degree of kinetic energy is necessary which is generated by heating the labelling precursor volume int eh synthesis apparatus 20 to a suitable temperature. For DOTATOC, for example, the optimum temperature is equal to/greater than 95° C.

The pH value of the labelling precursor in the labelling vessel 21 is in the range from 2 to 5. For the radiopharmaceutical $^{68}$Ga DOTATOC a preferred pH value is, for example 2.3.The pH value is set by the volume of water and labelling precursor, preferably without a buffer solution, and of the added HCl/acetone or HCl/ethanol solution or analogous systems. But it is also possible to set the pH value with the help of a buffer solution or, for example, HEPES, which can result in a modified optimum pH value.

The quantity of the labelling precursor from a ligand or a peptide or protein cross-linked in a covalent manner with a ligand, for example DOTATOC, in the labelling vessel 21, amounts to roughly 1 to 100 nmol, preferably 7 to 14 nmol, to which is added a corresponding volume of water and/or buffer or HEPES or analogous systems in order to set the pH value.

After the completed labelling of he labelling precursor with the purified $^{68}$Ga fraction to form the radiopharmaceutical, the conveyance apparatus 8, which contains no liquid, is operated in such a manner with the 3-way valve 13 open, that through the conduit 24 from the labelling vessel 13 closes the conduit 24 and opens conduit 25 which leads into the reservoir 18—or optionally into another reservoir, not shown. By operating the conveyance apparatus 9, the cartridge 11 is washed with pure water or analogous solvents which elute the free $^{68}$Ga or other, non-labelled $^{68}$Ga species, and discharge them in a manner not shown, for example back into the labelling vessel 21 which is now no longer needed.

Then, by operating the conveyance apparatus 10, which contains less than 0.5 ml ethanol or analogous solvent, the radiopharmaceutical is eluted, for example $^{68}$Ga DOTATOC, from the cartridge 11 and is fed into the reservoir 18 which contains an isotonic physiological sodium chloride solution. Alternatively, the specified fraction can also be eluted into an empty reservoir 18 which in principle permits the removal of the ethanol or analogous solvent.

Then the 3-way valve 13 closes the conduit 25 and by means of a device not shown the radiopharmaceutical is drawn through the conduit 26 from the reservoir 18 and fed through a filter 16 into the product vessel 17. A sterile filtering is provided by the filter 16 so that the radiopharmaceutical is ready for use thereafter.

The binding of the $^{68}$Ga to the labelling precursor amounts to more than 75% in reference to the decay-corrected activity of he initial $^{68}$Ge/Ga generator eluate. For example, the reactivity of the labelling precursor amounts to as much as 80%, 90% and more than 95% for 10 mCi of the $^{68}$Ge/Ga generator eluate after one, five and ten minutes.

The duration of the method from the introduction of the initial generator eluate to the supply of the radiopharmaceutical amounts to roughly 20 min.

Underpressure can be applied to ten conveyance apparatuses 2 to 10 and the conduits connected to them to transport the solutions through the conduits.

Of course, the whole process of the device is completely automated and is controlled, for example, by a computer program.

Especially for the imaging of neuroendocrine tumors with labelling reagents such as [$^{68}$Ga]DOTA-DPhe$^{1}$-Tyr$^{3}$-octreotide ([$^{68}$Ga]DOTATOC) and PET or analogous compounds with modified chelators or modified peptide amino acid sequences, since roughly year 2000 an outstanding new application of the $^{68}$Ge/Ga generator eluates has appeared which are used as tumor targeting vectors. The octapeptide octreotide has a high degree of affinity to the sstr2 subtype of human somatostatin receptor expressing tumors, and the conjugated macrocyclical bifunctional chelator DOTA binds the trivalent $^{68}Ga^{3+}$ coordinatively with greater thermodynamic and kinetic stability in vivo as well. Despite the relatively short half-life of the $^{68}$Ga, this type of $^{68}$Ga labelled compounds permits an excellent visualization of tumors and small metastases. This approach to tumor targeting with $^{68}$Ga can possibly be expanded to include a large number of other tumors, whereby then other peptides are employed.

$^{68}$Ga also finds applications in the myocardial perfusion diagnostics in the form of [$^{68}$Ga]BAT-TECH complex as perfusion tracer. This shows that basically every type of $^{68}$Ga labelling by means of ligand structures as a whole are applicable for nuclear medicine diagnostics, or will be in the future.

The "kit" type synthesis equally offers a further advantage such as the use of PET independent of an in-house direct production of established positron emitters such as $^{18}$F.

Parallel with this, there is currently an intensive improvement in molecular imaging by the combination of PET and computer tomography which also enlarges the application potential of $^{68}$Ga labelled imaging tracers. For these reasons the availability of optimized $^{68}$Ge/Ga generator systems is becoming more and more significant. The effective production of the $^{68}$Ge has currently assumed a key role under radiochemical and economic aspects.

An interesting and potentially significant application of the $^{68}$Ga without labelling chemistry is in the field of $^{68}$Ga-filled angioplasty containers for the inhibition of arterial restenosis after coronary angioplasty. This application of higher energy positron emitters follows the known applications with $^{188}$Re and other medium- and high-energy β emitters. Since here the liquid $^{68}$Ga eluate is used, minimum volumes of the $^{68}$Ge/Ga generator eluates offer optimum prerequisites.

The device is also suitable for concentrating and purifying radiogallium solutions. It is also suitable for purification, for volume reduction of gallium radioisotopes and for the labelling of labelling precursors with the $^{66}$Ga or $^{67}$Ga radioisotope.

Of course the device is also suitable for labelling ligands or a peptide or protein covalently cross-linked with a ligand with a radionuclide other than $^{68}$Ga. One example of this is $^{90}$Y, for which the eluate must be purified of other metals.

LIST OF REFERENCE NUMERALS AS USED HEREIN

1 refers to a $^{68}$Ge/Ga generator;
2 refers to a conveyance apparatus;
3 through 7 refer independent to conveyance apparatuses, such as a pump, syringe or piston;
8 through 10 refer independent to conveyance apparatuses, such as a pump, syringe or piston;
11 refers to a cartridge;
12 and 13 refer to 3-way values;
14 refers to a cation exchanger;
15 refers to a 3-way value;
16 refers to a filter;
17 refers to a product vessel;
18 refers to a reservoir;
19 refers to a waste vessel;
20 refers to a synthesis apparatus;
21 refers to a labelling vessel;
22 refers to a heating unit;
23 through 26 refer to conduits; and
27 refers to a table.

The invention claimed is:

1. Method for isolating a $^{68}$Ga radionuclide from a $^{68}$Ge/Ga generator eluate which contains $^{68}$Ga in ionic form, said method comprising feeding the $^{68}$Ge/Ga generator eluate directly into an exchanger and absorbing $^{68}$Ga quantitatively on the exchanger, and simultaneously chemically and radiochemically purifying the $^{68}$Ga and combining the $^{68}$Ga radionuclide with a labelling precursor comprising a ligand to form a radiopharmaceutical, wherein the exchanger is a cation exchanger and the cation exchanger is a highly acidic cation exchanger comprising a matrix from the group of polystyrene/divinylbenzene (DVB) resins, with a DVB concentration from 2 to over 20% in reference to cross-linked polymers of the resins and the matrix of the cation exchanger is loaded with $^{68}$Ga.

2. Method according to claim 1, wherein the $^{68}$Ga radionuclide is combined with a labelling precursor from a ligand or peptide or protein cross-linked in a covalent manner with a ligand into a radiopharmaceutical.

3. Method according to claim 1, wherein several $^{68}$Ge/Ga radionuclide generators are simultaneously or sequentially eluted and the common initial eluates are transferred to the cation exchanger.

4. Method according to claim 3, wherein $^{68}$Ge/Ga generators remain in operating condition if their initial $^{68}$Ga-eluate contains 50 or more mCi $^{68}$Ge.

5. Method according to claim 1, wherein the initially eluated $^{68}$Ge is not adsorbed, and a chemical purification of the $^{68}$Ga takes place on the cation exchanger during which the radiochemical $^{68}$Ge contamination is reduced to a value less than $10^{-8}$ percent.

6. Method according to claim 5, wherein the purifying step comprises acidic solutions of HCl/acetone or HCl/ethanol or analogous systems and the purification elutes chemical contaminants selected from one or more of Fe(III) and Zn(II) from the cation exchanger.

7. Method according to claim 5, wherein during the elution processes of $^{68}$Ga a substantial separation of initially eluted Ti(IV) occurs.

8. Method according to claim 1, wherein the purified and volume-reduced $^{68}$Ga radionuclide is directly eluted into a labelling vessel in which the labelling precursors and a solution comprising pure water or buffer systems have been introduced.

9. Method according to claim 8, wherein the labelling precursor introduced into the labelling vessel comprises a ligand or a peptide or protein covalently cross-linked with a ligand or other compounds in a quantity of about 1 to 100 nmol.

10. Method according to claim 9 wherein the labelling precursor comprises a ligand or a peptide or protein covalently cross-linked with a ligand or other compounds in a quantity of about 7 to 14 nmol.

11. Method according to claims 8 , wherein the bonding of the $^{68}$Ga to the labelling precursor amounts to more than 75% in relation to the decay-corrected activity of the initial $^{68}$Ge/Ga generator eluate.

12. Method according to claim 8, wherein the radiopharmaceutical from the labelling vessel is transferred to a cartridge onto which the radiopharmaceutical is fixed and the free $^{68}$Ga and/or other $^{68}$Ga species is eluated from the cartridge.

13. Method according to claim 12, wherein the cartridge is washed with a liquid and is purified of free $^{68}$Ga and/or other $^{68}$Ga species.

14. Method according to claim 13, wherein the cartridge is washed with water or analogous systems.

15. Method according to claim 12, wherein the radiopharmaceutical is eluated with less than 0.5 ml ethanol or analogous systems.

16. Method according to claim 12, wherein the radiopharmaceutical from the cartridge is eluated into an empty vessel for subsequent individual processes or into a vessel with a corresponding volume of isotonic physiological sodium chloride solution, and the eluted radiopharmaceutical sterile filtered and made available for use.

17. Method according to claim 8, wherein the pH value of the solutions for synthesizing the radiopharmaceutical in the labelling vessel is set to a value of 2.0 to 5.0 and only water or buffer systems or HEPES solutions are used.

18. Method according to claim 17, wherein the pH value of the solutions for synthesizing the radiopharmaceutical in the labelling vessel is set to a value of 2.3.

19. Method according to claim 1, wherein the purified and volume-reduced $^{68}$Ga radionuclide is directly eluted into a labelling vessel.

20. Method according to claim 1, wherein the labelling precursor contains a ligand from the group of chelators with sufficient thermodynamic and kinetic stability for the formation of the corresponding Ga ligand complexes.

21. Method according to claim 20, wherein the ligand is selected from DTPA, DOTA, NOTA, DFO and derivates thereof.

22. A method for the concentration and purification of gallium isotope solutions comprising the method according to claim 1.

23. A method for the purification, the volume reduction of gallium radioisotopes and labelling of precursors with the $^{66}$Ga or $^{67}$Ga radioisotope comprising the method according to claim 1.

24. Method for extracting a $^{68}$Ga radionuclide from a $^{68}$Ge/Ga generator eluate which contains $^{68}$Ga in ionic form along with Ti, Fe (III) and Zn (II) contaminants, said method comprising feeding generator eluate into a cation exchanger comprising sulphonic acid groups, said cation exchanger absorbing $^{68}$Ga, Fe (III), Zn (II) and Ti onto the exchanger from the $^{68}$Ge/Ga generator eluate and removing the exchanger-eluate comprising the $^{68}$Ga fraction;

eluting the Fe (III) and Zn (II) from the cation exchanger via a first acidic solution into a waste vessel;

eluting the $^{68}$Ga from the cation exchanger via a second acidic solution into a labeling vessel;

flushing with compressed air to collect $^{68}$Ga residues and feed them into the labeling vessel;

forming a $^{68}$Ga-labelled radiopharmaceutical by labeling the purified $^{68}$Ga within the labeling vessel with a labeling precursor;

filtering the $^{68}$Ga-labelled radiopharmaceutical through a sterile filter into a product vessel for use thereafter, and flushing residues of the Ti remaining on the cation exchanger into a waste vessel;

wherein said method is performed in about 20 minutes.

25. Method according to claim 1, said method further eluting Fe (Ill) from the cation exchanger.

26. Method according to claim 1, wherein the labelling precursor has a pH value of from 2 to 5.

* * * * *